(12) United States Patent
Bayer et al.

(10) Patent No.: US 10,420,896 B2
(45) Date of Patent: Sep. 24, 2019

(54) DRIVE MECHANISM OF A DRUG DELIVERY DEVICE

(71) Applicant: Sanofi, Paris (FR)

(72) Inventors: Stefan Bayer, Würselen (DE); Wolfgang Pelzer, Kreuzau (DE); Björn Wilden, Simmerath (DE); Philipp Zeitz, Aachen (DE)

(73) Assignee: Sanofi, Paris (FR)

( * ) Notice: Subject to any disclaimer, the term of this patent is extended or adjusted under 35 U.S.C. 154(b) by 416 days.

(21) Appl. No.: 14/916,818

(22) PCT Filed: Sep. 8, 2014

(86) PCT No.: PCT/EP2014/069036
§ 371 (c)(1),
(2) Date: Mar. 4, 2016

(87) PCT Pub. No.: WO2015/036345
PCT Pub. Date: Mar. 19, 2015

(65) Prior Publication Data
US 2016/0193424 A1 Jul. 7, 2016

(30) Foreign Application Priority Data

Sep. 10, 2013 (EP) .................................. 13183652

(51) Int. Cl.
*A61M 5/315* (2006.01)
*A61M 5/20* (2006.01)
*A61M 5/24* (2006.01)

(52) U.S. Cl.
CPC .......... *A61M 5/31553* (2013.01); *A61M 5/20* (2013.01); *A61M 5/24* (2013.01);
(Continued)

(58) Field of Classification Search
CPC ...... A61M 5/20; A61M 5/24; A61M 5/31553; A61M 5/31511; A61M 5/31535;
(Continued)

(56) References Cited

U.S. PATENT DOCUMENTS 9,022,994 B2 * 5/2015 Moser ............... A61M 5/31553
604/218
2005/0055011 A1 3/2005 Enggaard
(Continued)

FOREIGN PATENT DOCUMENTS

JP 2008-043761 2/2008
JP 2008-532581 8/2008
(Continued)

OTHER PUBLICATIONS

International Preliminary Report on Patentability in International Application No. PCT/EP2014/069036, dated Mar. 15, 2016, 9 pages.
(Continued)

*Primary Examiner* — Kevin C Sirmons
*Assistant Examiner* — Tezita Z Watts
(74) *Attorney, Agent, or Firm* — Fish & Richardson P.C.

(57) ABSTRACT

A drive mechanism of a drug delivery device for dispensing of a dose of a medicament, includes an elongated housing extending in an axial direction, a piston rod to operably engage with a piston of a cartridge to displace the piston in axial distal direction, a drive sleeve rotatably supported in the housing at least in a dose incrementing direction against the action of a spring element, and a ratchet mechanism to rotatably fix the drive sleeve relative to the housing. A first ratchet body has a first and a second ratchet element to alternately engage with a toothed profile of a second ratchet body. One of the first and second ratchet bodies is operably engaged with the housing and wherein the other one of the first and second ratchet bodies is operably engaged with the drive sleeve.

20 Claims, 8 Drawing Sheets

(52) U.S. Cl.
CPC ...... *A61M 5/3157* (2013.01); *A61M 5/31511* (2013.01); *A61M 5/31535* (2013.01); *A61M 5/31541* (2013.01); *A61M 5/31583* (2013.01); *A61M 2005/2026* (2013.01); *A61M 2005/2403* (2013.01)

(58) Field of Classification Search
CPC ............ A61M 5/31541; A61M 5/3157; A61M 5/31583; A61M 2005/2026; A61M 2005/2403
See application file for complete search history.

(56) References Cited

U.S. PATENT DOCUMENTS

| | | | |
|---|---|---|---|
| 2007/0129687 A1* | 6/2007 | Marshall | A61M 5/20 604/207 |
| 2008/0071227 A1* | 3/2008 | Moser | A61M 5/31553 604/207 |
| 2008/0108953 A1 | 5/2008 | Moser et al. | |
| 2012/0083746 A1 | 4/2012 | Markussen | |
| 2012/0296276 A1 | 11/2012 | Nicholls et al. | |

FOREIGN PATENT DOCUMENTS

| | | | |
|---|---|---|---|
| JP | 2009-153985 | 7/2009 | |
| WO | WO 2003/008023 | 1/2003 | |
| WO | WO2006/126902 | 11/2006 | |
| WO | WO 2006126902 A1 * | 11/2006 | ........ A61M 5/31553 |
| WO | WO-2006126902 A1 * | 11/2006 | ........ A61M 5/31553 |
| WO | WO2007/017052 | 2/2007 | |
| WO | WO2013/119132 | 8/2013 | |

OTHER PUBLICATIONS

International Search Report and Written Opinion in International Application No. PCT/EP2014/069036, dated Sep. 30, 2014, 13 pages.

* cited by examiner

A-A

B-B

C-C

D-D

DRIVE MECHANISM OF A DRUG DELIVERY DEVICE

CROSS-REFERENCE TO RELATED APPLICATIONS

This application is a U.S. national stage application under 35 USC § 371 of International Application No. PCT/EP2014/069036, filed on Sep. 8, 2014, which claims priority to European Patent Application No. 13183652.0, filed on Sep. 10, 2013, the entire contents of which are incorporated herein by reference.

TECHNICAL FIELD

The present disclosure relates to a drive mechanism for a drug delivery device and to a respective drug delivery device. In particular, the disclosure relates to an injection device such like a pen-type injector inter alia comprising a single and/or a last-dose limiting mechanism.

BACKGROUND

Drug delivery devices for setting and dispensing a single or multiple doses of a liquid medicament are as such well-known in the art. Generally, such devices have substantially a similar purpose as that of an ordinary syringe.

Drug delivery devices, in particular pen-type injectors have to meet a number of user-specific requirements. For instance, with patient's suffering chronic diseases, such like diabetes, the patient may be physically infirm and may also have impaired vision. Suitable drug delivery devices especially intended for home medication therefore need to be robust in construction and should be easy to use. Furthermore, manipulation and general handling of the device and its components should be intelligible and easy understandable. Moreover, a dose setting as well as a dose dispensing procedure must be easy to operate and has to be unambiguous.

Typically, such devices comprise a housing or a particular cartridge holder, adapted to receive a cartridge at least partially filled with the medicament to be dispensed. The device further comprises a drive mechanism, usually having a displaceable piston rod which is adapted to operably engage with a piston of the cartridge. By means of the drive mechanism and its piston rod, the piston of the cartridge is displaceable in a distal or dispensing direction and may therefore expel a predefined amount of the medicament via a piercing assembly, which is to be releasably coupled with a distal end section of the housing of the drug delivery device.

The medicament to be dispensed by the drug delivery device is provided and contained in a multi-dose cartridge. Such cartridges typically comprise a vitreous barrel sealed in distal direction by means of a pierceable seal and being further sealed in proximal direction by the piston. With reusable drug delivery devices an empty cartridge is replaceable by a new one. In contrast to that, drug delivery devices of disposable type are to be entirely discarded when the medicament in the cartridge has been completely dispensed or used-up.

Document WO 2006/076921 A1 describes a handheld mechanical injection device, wherein the medicament is expelled through an injection needle by release of a power reservoir in the device. The power reservoir is fully or partially released by actuation of a user operable release member being positioned at or near an upper end of the injection device. The power reservoir is arranged between the housing of the device and a dose setting member in such a way that when the dose setting member is rotated, energy is accumulated in the power reservoir.

The power reservoir comprises a torsion spring formed as a helical spring extending coaxially with an associated piston rod. The torsion spring is energized by rotating a ratchet which is operatively connected to the housing of the injection device when the dose to be injected is being set. In a dose setting position the ratchet is operatively connected with a housing part via a ratchet arm. Energy accumulated in the torsion spring is released by displacing the ratchet axially whereby it is released from its connection with the housing part in that the ratchet arm is moved into the housing part whereby the piston rod is allowed to rotate thereby expelling a set dose of medicament.

The torsion spring in combination with a ratchet allows to accumulate and to store mechanical energy in the device upon setting of a dose. However, if a set dose is too large a dose correction or dose decrementing operation is required. In order to enable dose correction or dose decrementing the ratchet must either temporally disengage or must be transiently overruled. Moreover, a dose decrementing actuation may act in unison with the biased spring element which may have a negative impact on the general handling of the device and its operability to modify the size of a dose.

Additionally, demands for dosing accuracy may further require that the ratchet successively engages with every standard unit of the medicament to be dispensed. Since typical handheld drug delivery devices are limited in geometrical size the mutually inter-engaging components of such a ratchet have to be rather small and filigree in order to provide a required dosing accuracy. However, such tiny or filigree mechanical components impose a rather complicated assembly process and may be rather susceptible to mechanical loads or to mechanical stress when the device is operated.

SUMMARY

In certain aspects of the present invention a drive mechanism of a drug delivery device can allow for a rather easy and intuitive setting and dispensing of a well-defined dose of a medicament. Certain aspects relate to an easy and intuitive dose setting as well as a respective dose correcting operation of the drive mechanism.

Additionally, in certain aspects, the drive mechanism can be rather robust and insensitive to externally applied mechanical loads or stress. Moreover, the drive mechanism can be easy to assemble and should exhibit a large degree of reliability.

In certain aspects of the invention a drug delivery device includes such a drive mechanism and includes a cartridge sealed with a piston to become operably engaged with a piston rod of such a drive mechanism.

In a first aspect a drive mechanism of a drug delivery device is provided for dispensing of a dose of a medicament. The drive mechanism comprises an elongated housing extending in an axial direction. Typically, the housing is of substantially tubular or cylindrical shape that allows gripping and operating of the drive mechanism or of the entire drug delivery device by one hand of a user.

The drive mechanism further comprises a piston rod to operably engage with a piston of a cartridge containing the medicament to be dispensed by the drive mechanism. The cartridge comprises a piston, which, by means of a displacement in axial distal direction, serves to expel an amount of the medicament from the cartridge that corresponds to the axial displacement of the piston. Typically, the piston seals the cartridge in axial proximal direction. The piston rod of the drive mechanism is operable to displace the piston of the cartridge in an axial distal direction. The piston rod is therefore operable to apply distally directed thrust or pressure to the piston of the cartridge for displacing the piston in distal direction relative to the cartridge for dispensing of a predefined amount of the medicament from the cartridge.

The drive mechanism further comprises a drive sleeve that is rotatably supported in the housing and which is typically operably releasable from the piston rod for setting of a dose. Typically, for dose setting the drive sleeve is rotatable relative to the housing in a dose incrementing direction against the action of a spring element. Since the drive sleeve is operably disconnected or disengaged from the piston rod during a dose setting procedure the piston rod remains substantially stationary with respect to the housing while the drive sleeve is rotated in dose incrementing direction against the action of the spring element.

During such a dose incrementing rotation of the drive sleeve the spring element is biased or strained in order to accumulate and to store mechanical energy. During a subsequent dose dispensing procedure the drive sleeve is driven by the relaxing spring element in an opposite, hence in a dose decrementing direction. Moreover, during dose dispensing the drive sleeve is operably connected or operably coupled with the piston rod for driving the piston rod in distal direction in order to dispense a previously set dose of the medicament from the cartridge. During dose dispensing the drive sleeve is operable to exert a driving force or a driving momentum to the piston rod. The driving force or the driving momentum is typically provided by the spring element previously biased during the dose setting procedure. In this way the drive mechanism is of semi-automated type. The user only has to trigger a dose dispensing action while the mechanical energy to drive the piston rod is exclusively provided by the biased spring element.

Additionally, the drive mechanism comprises a ratchet mechanism to rotatably fix the drive sleeve relative to the housing. By means of the ratchet mechanism mechanical energy is transferred to the spring element during setting of a dose. Furthermore, the mechanical energy can be stored and accumulated in the drive mechanism. It is only upon a dose dispensing action of the user, that the ratchet mechanism is released in order to switch the drive mechanism from a dose setting mode into a dose dispensing mode. In the dose dispensing mode, the drive sleeve is typically disengaged from the ratchet mechanism and is hence free to rotate under the action of the spring element, thereby transferring a driving force or a driving momentum to the piston rod.

The ratchet mechanism comprises a first ratchet body and a second ratchet body. First and second ratchet bodies are arranged in the elongated housing and are rotatable with respect to each other. It is the first ratchet body that has a first and a second ratchet element that are adapted to alternately engage with a toothed profile of the second ratchet body. In this way, the second ratchet body can be rotated relative to the first ratchet body in such a way, that first and second ratchet elements of the first ratchet body successively engage with the second ratchet body's toothed profile. Hence, the second ratchet body can be rotated relative to the first ratchet body in such a way, that the second ratchet body is rotatably secured to the first ratchet body at discrete steps.

Typically, the mutual engagement of first and second ratchet bodies provides an at least unidirectional rotation of the first ratchet body relative to the second ratchet body. Moreover, the first ratchet body is rotatable in dose incrementing direction relative to the second ratchet body in such a way, that first and second ratchet elements of the first ratchet body successively and/or sequentially engage with the toothed profile of the second ratchet body, thereby effectively preventing a self-actuated rotation of the second ratchet body in an opposite sense of rotation, hence in dose decrementing direction relative to the first ratchet body.

One of the first and second ratchet bodies is operably engaged or connected with the housing and the other one of the first and second ratchet bodies is operably engaged or connected with the drive sleeve. First and second ratchet bodies may also be integrally formed with the housing and/or with the drive sleeve and may therefore represent a portion of the housing and/or of the drive sleeve, respectively.

Since the first ratchet body comprises at least two, namely a first and a second ratchet element operable to alternately engage with the toothed profile of the second ratchet body a rather precise, fine-tuned or fine-adjustable ratchet mechanism can be provided that allows to implement comparatively small discrete steps of rotation without the necessity to minimize the geometric dimensions of the toothed profile and the first ratchet body's ratchet elements. By positioning first and second ratchet elements of the first ratchet body at a predefined offset in regard to the toothed profile of the second ratchet body an alternating mutual engagement of first and second ratchet elements with the toothed profile can be provided.

According to a further embodiment, the first ratchet body comprises a first ratchet member and a second ratchet member, wherein the first ratchet member supports the first ratchet element and wherein the second ratchet member supports the second ratchet element. First and second ratchet elements may be integrally formed with respective first and second ratchet members. Hence, the first and/or second ratchet elements may represent a particular portion of the respective ratchet member that directly engages with the second ratchet body.

Moreover, the first and/or the second ratchet elements may also comprise separate pieces or components displaceably or rotatably assembled to respective first and/or second ratchet members. Generally, by providing first and second ratchet elements on different ratchet members, a well-defined alternating engagement of the respective ratchet elements with the second ratchet body can be implemented.

According to another embodiment, the first and the second ratchet elements of first and second ratchet members are located at opposite circumferential end sections of the ratchet members. The ratchet members typically extend along the annular shaped toothed profile of the second ratchet body. Consequently, each or at least one the first and second ratchet members may comprise a ratchet arm of semi-circular or arched shape. The respective ratchet element typically extends radially inwardly or radially outwardly from the semi-circular or arc-shaped ratchet member in order to engage with the toothed profile of the second ratchet body.

Typically, when the first ratchet body is radially confined or is circumferentially surrounded by the second ratchet body, first and second ratchet elements of the first ratchet body extend radially outwardly to engage with a radially inwardly facing toothed profile of the second ratchet body. In other embodiments it is also conceivable, that the second ratchet body is located radially inside the first ratchet body. Then, the first and second ratchet elements of the first ratchet body extend radially inwardly to alternately engage with the toothed profile of the first ratchet body located on the outer circumference thereof. By providing first and second ratchet elements at opposite circumferential end sections of first and second ratchet members, respective oppositely located portions of the toothed profile of the second ratchet body may alternately engage with the first ratchet body and with its first ratchet member. By arranging alternately engaging first and second ratchet elements at opposite, in particular at diametrically opposite end sections of first and second ratchet members, the first ratchet element may engage with the toothed profile while the second ratchet element may substantially disengage from the toothed profile, and vice versa.

According to another embodiment, the position and geometrical shape of the ratchet elements is such that one of the ratchet elements of the first ratchet body is engaged with the toothed profile of the second ratchet body while the other one of the ratchet elements is effectively disengaged from the toothed profile and vice versa. In typical embodiments first and second ratchet elements of the first ratchet body's ratchet member are phase shifted with regard to the regular arrangement of the teeth of the toothed profile of the second ratchet body. Given that the various teeth of the toothed profile of the second ratchet body are separated by an angular distance L, first and second ratchet elements of the first ratchet body may be separated from each other by an angular distance n+L/2, wherein n represents an integer number of teeth of the toothed profile of the second ratchet body. In this way, a kind of 180°-phase shift between first and second ratchet elements in regard of the toothed profile can be realized.

Apart from a 180°- or pi phase shift also phase shifts of pi/4, pi/6 or pi/8 between first and second ratchet elements are conceivable. In this way dosing accuracy may be further enhanced and/or the step size of successive dosing steps can be further reduced or minimized.

According to a further embodiment at least one of the first and second ratchet members of the first ratchet body is pivotable and/or resiliently deformable in radial direction. Typically, at least one or both ratchet members is or are pivotable and/or resiliently deformable in radial direction against a restoring force. Said restoring force may emanate from the inherent flexibility of the ratchet member and/or of its ratchet elements. Alternatively, at least one ratchet member and/or its ratchet element may be pivotable in radial direction under the effect of a restoring element, such like a spring. In either way the pivotable and/or resilient support of the first and/or second ratchet member provides a rather self-actuated mutual engagement of the first and second ratchet elements with the toothed profile of the second ratchet body.

During a dose incrementing rotation of the drive sleeve relative to the housing and hence during a dose incrementing rotation of the first or second ratchet body relative to the second or first ratchet body at least one of the first and second ratchet members resiliently or flexibly deforms or pivots respectively as the toothed profile of the second ratchet body consecutively or alternately meshes with first and second ratchet elements of the first ratchet body. The successive and regular engagement of ratchet elements with the toothed profile further provides an audible feedback to the user, that e.g. a dose setting procedure is in progress and that the dose size increases or decreases by discrete steps. When implemented as a drug delivery device for dispensing of e.g. insulin, the discrete dosing steps determined by the ratchet mechanism may correspond to single international units IU of insulin.

According to another embodiment at least one of the first and second ratchet elements is adapted to block a rotation of the second ratchet body relative to the first ratchet body in a dose decrementing direction when a torque acting between first and second ratchet bodies is below a first predefined threshold. Given that a torque or a driving force below said first threshold is provided to the drive sleeve, the ratchet mechanism provides a unidirectional ratchet which allows only for a dose incrementing rotation of the drive sleeve but inhibits a counter-directed dose decrementing rotation thereof. The first predetermined threshold of the torque between first and second ratchet bodies is typically larger than the maximum torque that may be provided by the biased spring element.

In this way, the ratchet mechanism serves to inhibit and to interlock a self-actuated rotational displacement of the drive sleeve that may be driven by the strained spring element. In this way, mechanical energy transferred to the spring element can be accumulated in the spring element and can be safely stored in the drive mechanism by means of the ratchet mechanism.

This torque sensitive or torque dependent blocking of the second ratchet body's rotation is achievable by a specific geometric shape, by specific elastic or resilient properties of the first ratchet body and its first and second ratchet elements. The geometric shapes and elastic properties as well as the friction forces acting between the ratchet elements and the second ratchet body's toothed profile are selected and designed such that a holding force or holding torque acting between the first and second ratchet body is smaller than a torque provided by the biased spring element.

According to another embodiment at least one of the first and second ratchet elements is adapted to release a rotation of the second ratchet body relative to the first ratchet body in a dose decrementing direction when a torque acting between first and second ratchet bodies is equal or above the first predefined threshold. In this way, mutual engagement of first and/or second ratchet elements with the toothed profile of the second ratchet body is designed such, that application of a torque equal to or above the first predefined threshold may overrule the rotational interlock of the ratchet mechanism.

In this way, the ratchet mechanism also supports a dose decrementing rotation of the drive sleeve relative to the housing, which may be required for correcting of a set dose. The magnitude of the first threshold torque is determined by the flexibility of the first ratchet body's ratchet elements and/or by the flexibility of the first and/or second ratchet members and hence by the restoring force of the ratchet elements against radially directed pivoting displacement, further by the geometric shape of the ratchet element and the geometric shape of the corresponding toothed profile of the second ratchet body. Modifications of the geometry of the teeth of the toothed profile as well as modifications of the resilient or pivotable behaviour of the first ratchet body's ratchet elements or of its ratchet members may affect the torque threshold in either way.

By appropriately designing the geometry of mutually engaging toothed profile and ratchet elements and by making use of a well-defined pivotable or resiliently deformable behaviour of at least one of first and second ratchet members of the first ratchet body the first predefined threshold can be raised or lowered according to general requirements of the ratchet mechanism and the drive mechanism.

The geometric shapes and elastic properties as well as the friction forces acting between the ratchet elements and the second ratchet body's toothed profile are selected and designed such that a user induced dose decrementing rotation of the second ratchet body together with a torque provided by the biased spring element is larger than a holding force or holding torque acting between the first and second ratchet body.

According to another embodiment at least one of the first and second ratchet elements is alternatively or further adapted to apply a retarding force of predefined magnitude onto the second ratchet body when the second ratchet body rotates relative to the first ratchet body in dose incrementing direction and/or in dose decrementing direction. The first and/or the second ratchet element may also mesh with the toothed profile of the second ratchet body.

The geometric shapes and elastic properties as well as the friction forces acting between the ratchet elements and the second ratchet body's toothed profile are selected and designed such that the first and/or second ratchet elements apply a retarding force towards the second ratchet body of predefined magnitude.

According to a further embodiment first and second ratchet members are symmetrically shaped and/or are symmetrically arranged with respect to a longitudinal axis of the drive sleeve. Moreover, first and second ratchet members may be integrally formed and may be mutually interconnected. By having symmetrically shaped and/or symmetrically arranged first and second ratchet members, substantially oppositely located portions of the toothed profile of the second ratchet body may alternately or simultaneously engage with the ratchet elements of first and second ratchet members.

Moreover and in general also first and second ratchet elements comprise substantially equal geometry and may be symmetrically arranged with regard to the longitudinal axis extending through the first ratchet body.

According to another embodiment, the first ratchet elements and/or the second ratchet elements are arranged at geometrically opposite portions of the second ratchet body's toothed profile. Since the first and second ratchet elements are of substantially equal shape and geometry a substantially equally alternating engagement with the toothed profile can be provided as the first and second ratchet bodies mutually rotate in either dose incrementing or dose decrementing direction. In particular, the first and second ratchet elements may alternately engage with the toothed profile and may be positioned relative to each other at a circumferential offset of n+L/2.

According to another embodiment the first ratchet element is phase shifted to the second ratchet element with regard to the period of the toothed profile of the second ratchet body. In this way, first and second ratchet elements may alternately engage or may alternately mesh with the toothed profile of the second ratchet body. Phase shifts between first and second ratchet elements may be around 180° with regard to the period of teeth of the the second ratchet body's toothed profile.

In still another embodiment the first and second ratchet bodies are axially displaceable relative to each other to selectively engage and to selectively disengage first and second ratchet bodies.

Typically, first and second ratchet bodies are mutually engaged by means of the toothed structure and by means of the first and second ratchet elements when the drive mechanism is in a dose setting mode. In this configuration the drive sleeve is disengaged from the piston rod and may therefore be rotated in dose incrementing as well as in dose decrementing direction for setting of a dose.

By axially displacing the drive sleeve relative to the housing the drive sleeve operably engages with the piston rod in a torque or force transmitting way. By switching the drive mechanism from the dose setting mode into the dose dispensing mode also first and second ratchet bodies are axially displaced relative to each other in order to operably disengage. Due to this axial displacement of e.g. the second ratchet body relative to the housing and hence relative to the first ratchet body fixed to the housing the ratchet elements of the first ratchet body disengage from the toothed profile thereby enabling a rotation of the second ratchet body relative to the first ratchet body.

In this way also the drive sleeve may operably disengage from the housing of the drive mechanism thereby allowing the drive sleeve to rotate under the action of the previously strained spring element. Typically, axial displacement of first and second ratchet bodies relative to each other occurs against the action of a retaining spring element. The axial displacement of first and second ratchet bodies may be triggered by depressing of an actuation member of the drive mechanism, typically located at a proximal end of the housing. Depression of the actuation member typically occurs against the action of the retention spring element so that disengagement of first and second ratchet bodies requires a constant depression of the actuation member e.g. in axial distal direction.

The retention spring element serves to return the first and second ratchet bodies into a mutual engagement configuration as soon as the actuation member is no longer depressed by e.g. a thumb of a user. In this way, an early or premature release of the actuation member leads to a self-locking of the ratchet mechanism and hence of the drive mechanism by a mutual engagement of first and second ratchet bodies. In this way, mechanical energy stored in the spring element does not get lost and remains in the drive mechanism.

According to a further embodiment the first ratchet body is fixed to the housing or is integrally formed with the housing and comprises first and second ratchet elements e.g. extending radially inwardly from respective arc-shaped or semi-circular shaped ratchet members. The second ratchet body in turn is fixed to the drive sleeve or is integrally formed with the drive sleeve and comprises a radially outwardly extending toothed profile to mesh with first and second ratchet elements of the first ratchet body. In a configuration wherein first and second ratchet bodies are integrally formed with the housing and with the drive sleeve, respectively, first and second ratchet bodies only represent respective portions of the housing and of the drive sleeve. In this configuration the ratchet mechanism is directly implemented into the drive sleeve and into the housing without the necessity of providing any further mechanical components.

In an alternative embodiment the first ratchet body is fixed to the drive sleeve or is integrally formed with the drive sleeve and comprises radially outwardly extending first and second ratchet elements, typically extending from respective arc-shaped or semi-circular shaped ratchet members. Moreover, in this configuration the second ratchet body is fixed to the housing or is integrally formed with the housing and comprises a radially inwardly extending toothed profile. The toothed profile may be located on an inside facing portion of a sidewall of the tubular shaped housing whereas the radially outwardly extending ratchet elements of the first ratchet body are biased radially outwardly to mesh with the toothed profile.

Some aspects of the present invention also relate to a drug delivery device for dispensing of a dose of a medicament. The drug delivery device comprises a drive mechanism as described above and a cartridge at least partially filled with the medicament to be dispensed by the drug delivery. The cartridge is arranged in the housing of the drive mechanism or in a cartridge holder of the drug delivery device which is fixed to the housing either releasably or non-releasably. When designed as a disposable drug delivery device, the cartridge holder is non-releasably attached and fixed to the housing or body of the drug delivery device. Consequently, the drug delivery device comprises a cartridge holder to receive and to accommodate a cartridge filled with the medicament.

In the present context, the distal direction points in the direction of the dispensing and of the device, where, preferably a needle assembly is provided having a double-tipped injection needle that is to be inserted into biological tissue or into the skin of a patient for delivery of the medicament.

The proximal end or proximal direction denotes the end of the device or a component thereof, which is furthest away from the dispensing end. Typically, an actuating member is located at the proximal end of the drug delivery device, which is directly operable by a user to be rotated for setting of a dose and which is operable to be depressed in distal direction for dispensing of a dose.

The term "drug" or "medicament", as used herein, means a pharmaceutical formulation containing at least one pharmaceutically active compound, wherein in one embodiment the pharmaceutically active compound has a molecular weight up to 1500 Da and/or is a peptide, a proteine, a polysaccharide, a vaccine, a DNA, a RNA, an enzyme, an antibody or a fragment thereof, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exendin-3 or exendin-4 or an analogue or derivative of exendin-3 or exendin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des(B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N-(N-palmitoyl-Y-glutamyl)-des(B30) human insulin; B29-N-(N-lithocholyl-Y-glutamyl)-des(B30) human insulin; B29-N-(ω-carboxyheptadecanoyl)-des(B30) human insulin and B29-N-(ω-carboxyheptadecanoyl) human insulin.

Exendin-4 for example means Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu- Lys-Asn-Gly-Gly-Pro-Ser- Ser-Gly-Ala-Pro-Pro-Pro-Ser-NH2.

Exendin-4 derivatives are for example selected from the following list of compounds:

H-(Lys)4-des Pro36, des Pro37 Exendin-4(1-39)-NH2,
H-(Lys)5-des Pro36, des Pro37 Exendin-4(1-39)-NH2,
des Pro36 Exendin-4(1-39),
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(02)25, Asp28] Exendin-4(1-39),
des Pro36 [Met(O)14 Trp(02)25, IsoAsp28] Exendin-4(1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4 (1-39), wherein the group-Lys6-NH2 may be bound to the C-terminus of the Exendin-4 derivative;

or an Exendin-4 derivative of the sequence
des Pro36 Exendin-4(1-39)-Lys6-NH2 (AVE0010),
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4(1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4(1-39)-(Lys)6-NH2,
H-(Lys)6-des Pro36 [Trp(O2)25, Asp28] Exendin-4(1-39)-Lys6-NH2,
H-des Asp28 Pro36, Pro37, Pro38 [Trp(O2)25] Exendin-4(1-39)-NH2,
H-(Lys)6-des Pro36, Pro37, Pro38 [Trp(O2)25, Asp28] Exendin-4(1-39)-NH2,
H-Asn-(Glu)5-des Pro36, Pro37, Pro38 [Trp(O2)25, Asp28] Exendin-4(1-39)-NH2,
des Pro36, Pro37, Pro38 [Trp(O2)25, Asp28] Exendin-4 (1-39)-(Lys)6-NH2,
H-(Lys)6-des Pro36, Pro37, Pro38 [Trp(O2)25, Asp28] Exendin-4(1-39)-(Lys)6-NH2,
H-Asn-(Glu)5-des Pro36, Pro37, Pro38 [Trp(O2)25, Asp28] Exendin-4(1-39)-(Lys)6-NH2,
H-(Lys)6-des Pro36 [Met(O)14, Asp28] Exendin-4(1-39)-Lys6-NH2, des Met(O)14 Asp28 Pro36, Pro37, Pro38 Exendin-4(1-39)-NH2, H-(Lys)6-desPro36, Pro37, Pro38 [Met(O)14, Asp28] Exendin-4(1-39)-NH2, H-Asn-(Glu)5-des Pro36, Pro37, Pro38 [Met(O)14, Asp28] Exendin-4(1-39)-NH2, des Pro36, Pro37, Pro38 [Met(O)14, Asp28] Exendin-4(1-39)-(Lys)6-NH2, H-(Lys)6-des Pro36, Pro37, Pro38 [Met(0)14, Asp28] Exendin-4(1-39)-(Lys)6-NH2, H-Asn-(Glu)5 des Pro36, Pro37, Pro38 [Met(0)14, Asp28] Exendin-4(1-39)-(Lys)6-NH2, H-Lys6-des Pro36 [Met(O)14, Trp(O2)25, Asp28] Exendin-4(1-39)-Lys6-NH2, H-des Asp28 Pro36, Pro37, Pro38 [Met(O)14, Trp(O2)25] Exendin-4(1-39)-NH2, H-(Lys)6-des Pro36, Pro37, Pro38 [Met(O)14, Asp28] Exendin-4(1-39)-NH2, H-Asn-(Glu)5-des Pro36, Pro37, Pro38 [Met(O)14, Trp (02)25, Asp28] Exendin-4(1-39)-NH2, des Pro36, Pro37, Pro38 [Met(O)14, Trp(O2)25, Asp28] Exendin-4(1-39)-(Lys)6-NH2, H-(Lys)6-des Pro36, Pro37, Pro38 [Met(O)14, Trp(O2) 25, Asp28] Exendin-4(S1-39)-(Lys)6-NH2, H-Asn-(Glu)5-des Pro36, Pro37, Pro38 [Met(O)14, Trp (O2)25, Asp28] Exendin-4(1-39)-(Lys)6-NH2;

or a pharmaceutically acceptable salt or solvate of any one of the afore-mentioned Exendin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Antibodies are globular plasma proteins (~150 kDa) that are also known as immunoglobulins which share a basic structure. As they have sugar chains added to amino acid residues, they are glycoproteins. The basic functional unit of each antibody is an immunoglobulin (Ig) monomer (containing only one Ig unit); secreted antibodies can also be dimeric with two Ig units as with IgA, tetrameric with four Ig units like teleost fish IgM, or pentameric with five Ig units, like mammalian IgM.

The Ig monomer is a "Y"-shaped molecule that consists of four polypeptide chains; two identical heavy chains and two identical light chains connected by disulfide bonds between cysteine residues. Each heavy chain is about 440 amino acids long; each light chain is about 220 amino acids long. Heavy and light chains each contain intrachain disulfide bonds which stabilize their folding. Each chain is composed of structural domains called Ig domains. These domains contain about 70-110 amino acids and are classified into different categories (for example, variable or V, and constant or C) according to their size and function. They have a characteristic immunoglobulin fold in which two β sheets create a "sandwich" shape, held together by interactions between conserved cysteines and other charged amino acids.

There are five types of mammalian Ig heavy chain denoted by α, δ, ε, γ, and μ. The type of heavy chain present defines the isotype of antibody; these chains are found in IgA, IgD, IgE, IgG, and IgM antibodies, respectively.

Distinct heavy chains differ in size and composition; α and γ contain approximately 450 amino acids and δ approximately 500 amino acids, while p and E have approximately 550 amino acids. Each heavy chain has two regions, the constant region ($C_H$) and the variable region ($V_H$). In one species, the constant region is essentially identical in all antibodies of the same isotype, but differs in antibodies of different isotypes. Heavy chains γ, α and δ have a constant region composed of three tandem Ig domains, and a hinge region for added flexibility; heavy chains μ and ε have a constant region composed of four immunoglobulin domains. The variable region of the heavy chain differs in antibodies produced by different B cells, but is the same for all antibodies produced by a single B cell or B cell clone. The variable region of each heavy chain is approximately 110 amino acids long and is composed of a single Ig domain.

In mammals, there are two types of immunoglobulin light chain denoted by λ and κ. A light chain has two successive domains: one constant domain (CL) and one variable domain (VL). The approximate length of a light chain is 211 to 217 amino acids. Each antibody contains two light chains that are always identical; only one type of light chain, κ or λ, is present per antibody in mammals.

Although the general structure of all antibodies is very similar, the unique property of a given antibody is determined by the variable (V) regions, as detailed above. More specifically, variable loops, three each the light (VL) and three on the heavy (VH) chain, are responsible for binding to the antigen, i.e. for its antigen specificity. These loops are referred to as the Complementarity Determining Regions (CDRs). Because CDRs from both VH and VL domains contribute to the antigen-binding site, it is the combination of the heavy and the light chains, and not either alone, that determines the final antigen specificity.

An "antibody fragment" contains at least one antigen binding fragment as defined above, and exhibits essentially the same function and specificity as the complete antibody of which the fragment is derived from. Limited proteolytic digestion with papain cleaves the Ig prototype into three fragments. Two identical amino terminal fragments, each containing one entire L chain and about half an H chain, are the antigen binding fragments (Fab). The third fragment, similar in size but containing the carboxyl terminal half of both heavy chains with their interchain disulfide bond, is the crystalizable fragment (Fc). The Fc contains carbohydrates, complement-binding, and FcR-binding sites. Limited pepsin digestion yields a single F(ab')2 fragment containing both Fab pieces and the hinge region, including the H-H interchain disulfide bond. F(ab')2 is divalent for antigen binding. The disulfide bond of F(ab')2 may be cleaved in order to obtain Fab'. Moreover, the variable regions of the heavy and light chains can be fused together to form a single chain variable fragment (scFv).

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

It will be further apparent to those skilled in the art that various modifications and variations can be made to the present invention without departing from the spirit and scope of the invention. Further, it is to be noted, that any reference numerals used in the appended claims are not to be construed as limiting the scope of the invention.

BRIEF DESCRIPTION OF THE DRAWINGS

In the following, a brief description of the drawings is provided, in which.

DETAILED DESCRIPTION

Figure 6:
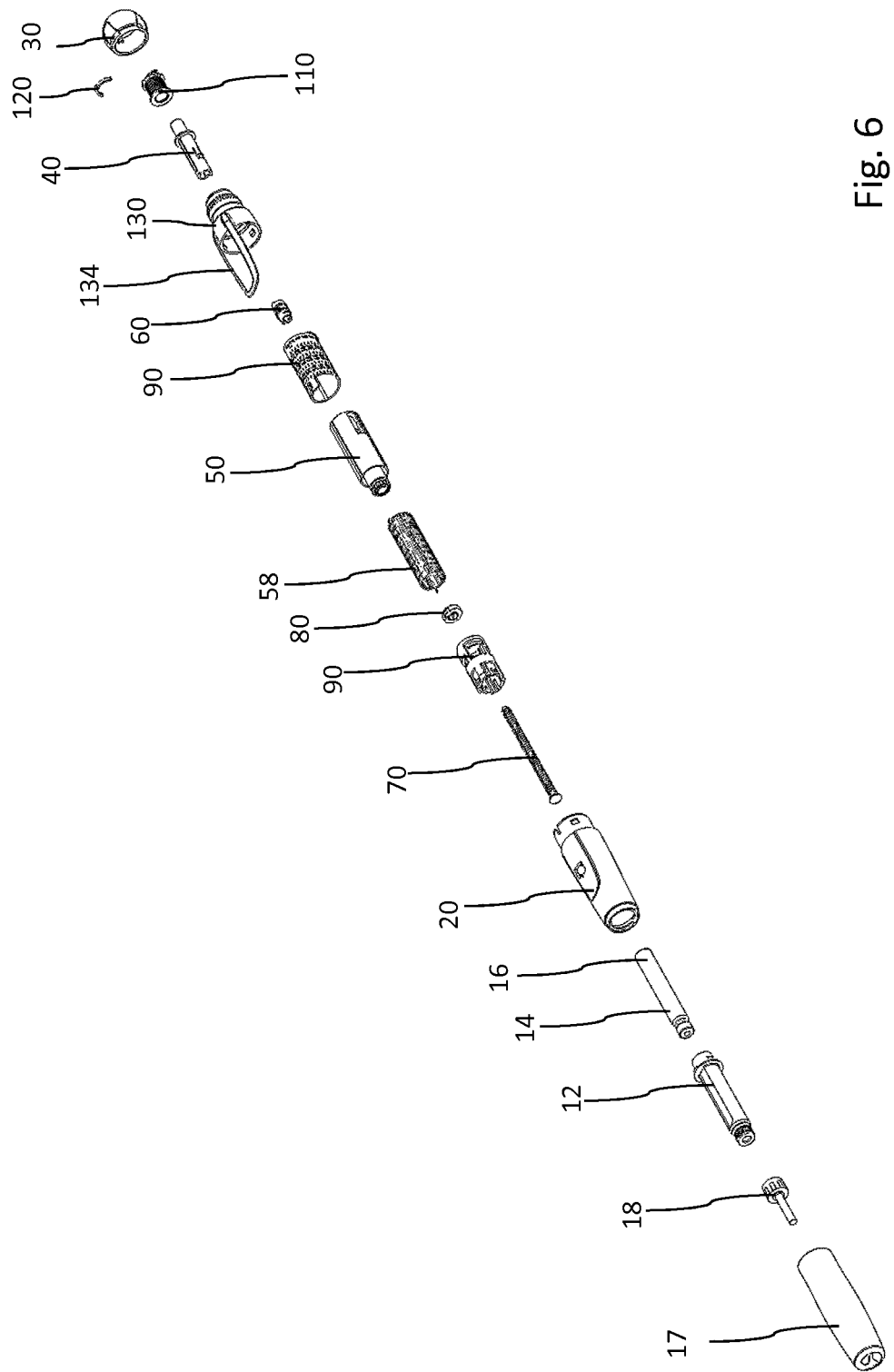
FIG. 6 is illustrative of an exploded view of the various components of the drug delivery device.

In FIG. 6, a particular embodiment of a drug delivery device 10 is illustrated in an exploded view. The drug delivery device 10 of pen-injector type and comprises a substantially cylindrical and axially elongated shape. Throughout the Figures, the axial distal direction is denoted with reference number 1 and the opposite proximal direction is denoted with reference number 2. The drug delivery device 10 which is also shown in an assembled configuration in FIG. 1 in longitudinal cross section comprises a drive mechanism 3 arranged in a proximal housing 20. In distal direction, the housing 20 is connected with a cartridge holder 12 which is adapted to accommodate and to receive a cartridge 14 containing the medicament to be dispensed by the drug delivery device 10. The cartridge 14 typically comprises a vitreous barrel of cylindrical shape which is sealed in distal direction by a pierceable sealing member, such like a septum.

In proximal direction 2, the cartridge 14 is sealed by a piston 16 slideably arranged in the vitreous barrel of the cartridge 14. Displacement of the piston 16 in distal direction 1 leads to a respective built-up of a fluid pressure inside the cartridge 14. When the distal outlet of a cartridge 14 is connected with e.g. a needle assembly 18, as for instance indicated in FIG. 1, a predefined amount of the liquid medicament contained in the cartridge 14 can be expelled and dispensed via an injection needle of the needle assembly 18, which is not particularly illustrated here.

Figure 1:
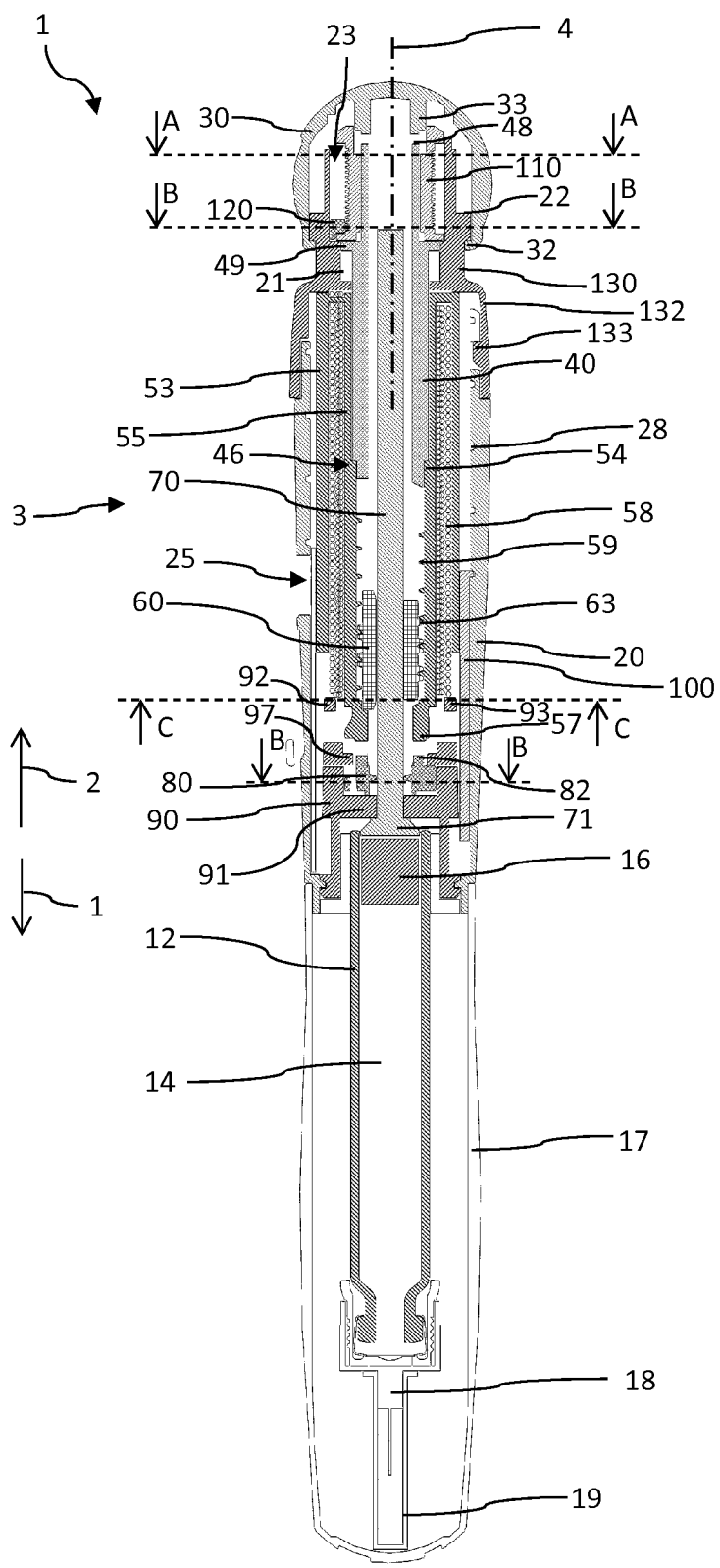
FIG. 1 schematically illustrates a pen-type injection device in a longitudinal cross section, FIG. 2 schematically shows a cross-section through the device according to FIG. 1 along A-A.

In FIG. 1, an inner needle cap 19 to protect the double-tipped injection needle is schematically indicated. The needle assembly 18 is typically arranged on a distal end portion of the cartridge holder 14. Typically, a distally located socket of the cartridge holder 12 and the needle assembly 18 comprise mutually corresponding threads to screw the needle assembly 18 onto the cartridge holder 12 in a releasable and removable way.

The cartridge holder 12 is to be protected and covered by a protective cap 17. Prior to setting and/or dispensing of a dose, the protective cap 17 as well as the inner needle cap 19 are to be removed. After dispensing or injecting of the medicament into biological tissue, the needle assembly 18 is typically to be discarded and the distal end of the drug delivery is to be covered by the protective cap 17.

The drive mechanism 3 as illustrated in an exploded view in FIG. 6 and as shown in cross section in FIG. 1 in its fully assembled configuration comprises numerous functional components by way of which a dose of variable size can be set and subsequently dispensed.

The dose dispensing procedure comes along with a distally directed advancing displacement of the piston rod 70 relative to the housing 20. The drive mechanism 3 therefore comprises at least a housing 20, a piston rod 70 and a drive sleeve 50 which can be released and operably engaged with the piston rod 70 for selectively setting and dispensing of a dose. Moreover, the drive mechanism 3 comprises a dose limiting member 60 which is engaged with the drive sleeve 50 as well as with the piston rod 70. Mutual engagement of the dose limiting member 60 with both, the drive sleeve 50 and with the piston rod 70 is such, that the dose limiting member is displaced in axial direction, hence in distal and/or proximal direction 1, 2 relative to the drive sleeve 50 when the drive sleeve 50 rotates relative to the piston rod 70 during a dose setting procedure.

Apart from the drive sleeve 50, the dose limiting member 60 and the piston rod 70, the drive mechanism 3 comprises a number of further components as illustrated in FIG. 1. These components together with the actuation member 30 as shown in inter alia serve to visually indicate the size of set dose to a user and further serve to transfer a rotational and/or axial displacement of the user-operated actuation member 30 into respective rotational and/or axial displacement of the drive sleeve 50 for dose setting and/or dose dispensing purpose.

It is to be noted here, the embodiments as illustrated in FIGS. 1 to 10 are only exemplary for one of a plurality of conceivable drive mechanisms that may be equipped with the single dose limiting mechanism as well as the last dose limiting mechanism according to certain aspects of the present invention.

In the following, setting of a dose is described.

Figure 7:
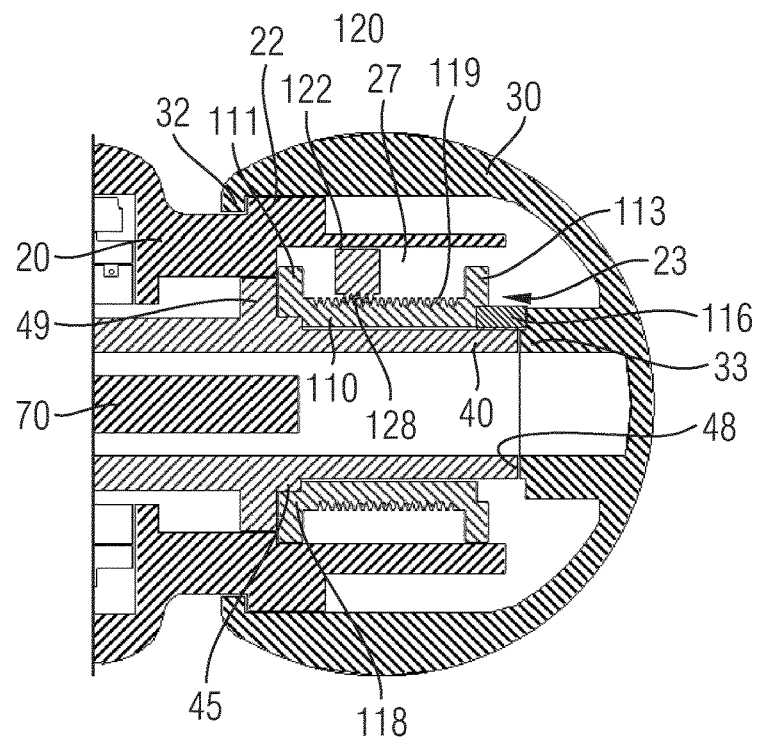
FIG. 7 shows a longitudinal cross-section through the proximal end of the device according to FIG. 1.
Figure 8:
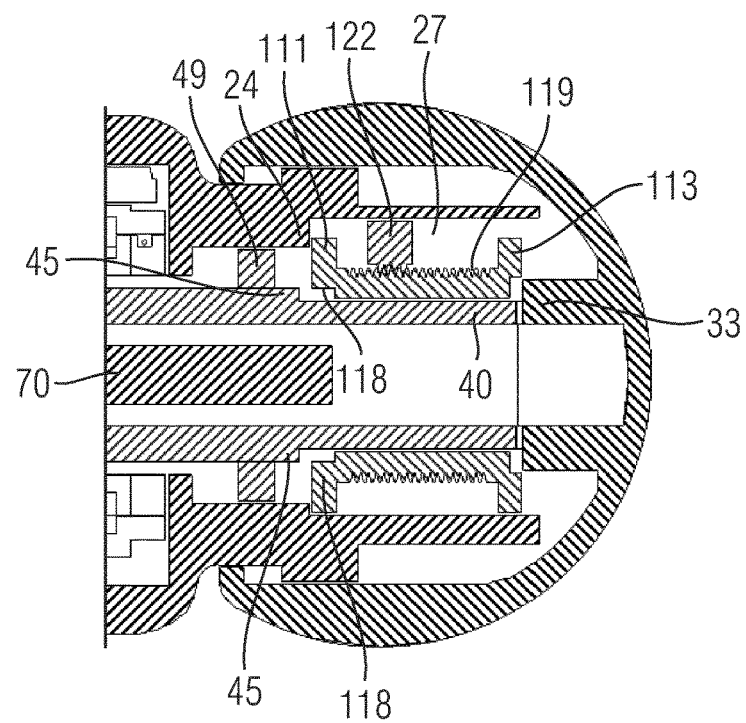
FIG. 8 shows the proximal end according to FIG. 7 with the actuation member depressed in distal direction.

For setting of a dose, the user grips the actuation member 30 located at the proximal end of the housing 20. The actuation member 30 comprises a radially inwardly extending flange portion 32 at its distal end as indicated in FIGS. 7 to 9, which in a proximally located configuration according to FIG. 7 axially abuts with a radially outwardly extending rim 22 of the housing 20.

The housing 20 further comprises a proximal and tubular shaped receptacle 23 to receive a substantially tubular shaped last dose sleeve 110. The last dose sleeve 110 comprises a radially outwardly extending distal flange 111 extending on a distal end thereof. With this distal flange 111 the last dose sleeve 110 abuts in distal direction with a radially inwardly extending socket 24 of the housing 20. Moreover, by means of the distal flange 111 the last dose sleeve 110 is also radially guided and confined in the proximal receptacle 23 of the housing 20.

Furthermore, by means of its flange portion 32 the actuation member 30 may be snapped on the proximal end of the housing 20 and may therefore positively engage with the housing 20 at least in proximal direction 2. In particular, the actuation member 30 is cup-shaped and surrounds and closes the receptacle 23 of the housing 20 in proximal direction when assembled thereon.

Figure 9:
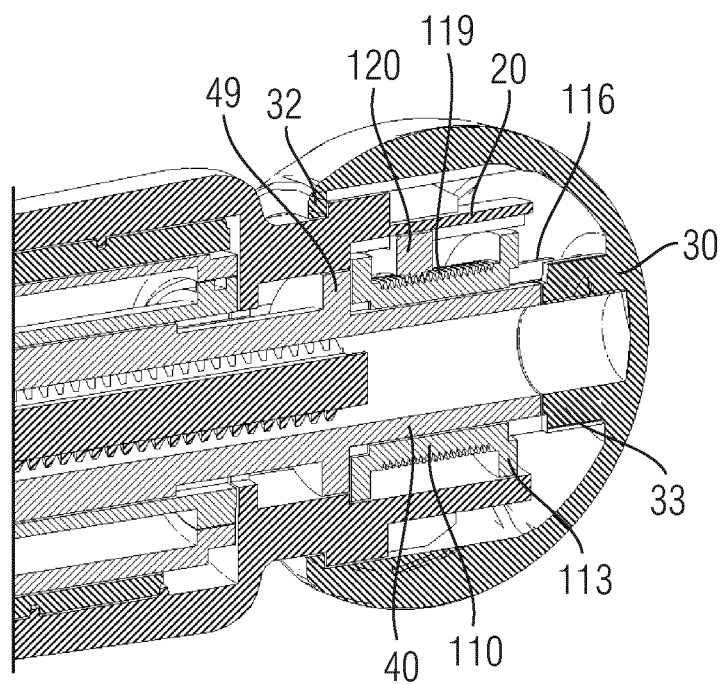
FIG. 9 shows a partially cut and perspective illustration of the proximal end of the drug delivery device and FIG. 10 shows a side view of the outer housing of the drug delivery device according to FIG. 1.

From a proximal portion of the last dose sleeve 110, there extend two helically shaped resilient spring elements 116 integrally formed with the last dose sleeve 110 as indicated in FIG. 9. These spring elements 116 abut with a proximal and inward facing portion of the hollow actuation member 30 and therefore keep the actuation member 30 in its initial, hence proximally located configuration as illustrated for instance in FIG. 7.

Figure 2:
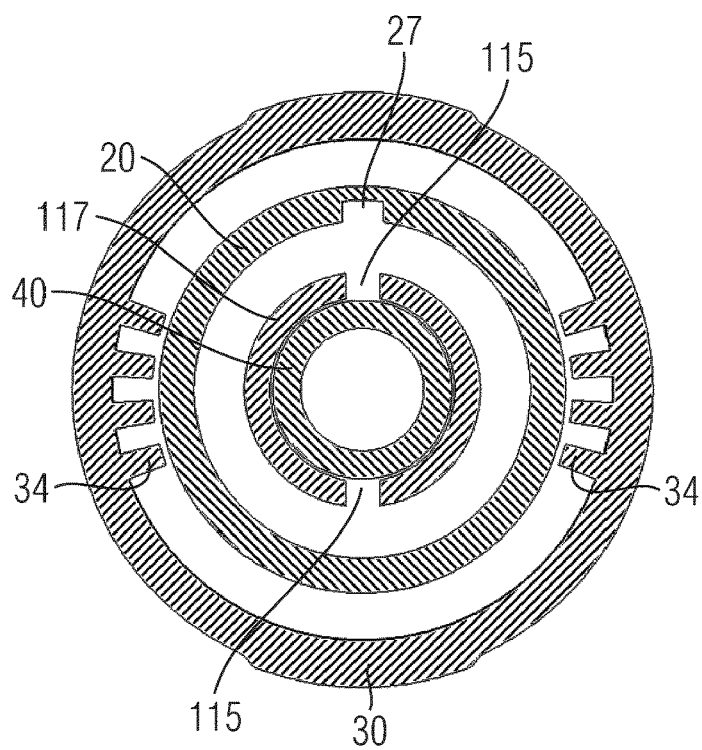

In this initial configuration which coincides with and specifies a dose setting mode of the drive mechanism 3, axially inwardly extending journals 33 of the actuation member 30 extend into two respective diametrically oppositely located recesses 115 of a proximal rim 117 of the last dose sleeve 110 as indicated in FIG. 2. In this way, the last dose sleeve 110 and the actuation member 30 are rotatably coupled in the initial configuration of the actuation member 30.

In this configuration, rotation of the actuation member 30 leads to a corresponding rotation of the last dose sleeve 110. In the dose setting mode, the last dose sleeve 110 is further rotatably engaged and rotatably coupled with a clutch 40 as becomes apparent from a combination of FIGS. 3 and 7. As in particular illustrated in the cross section B-B in FIG. 3, the inside facing portion of the distal end of the last dose sleeve 110 comprises a toothed surface 118 that meshes with radially outwardly extending teeth 45 of the clutch 40.

This way, the last dose sleeve 110 and the clutch 40 extending there through and hence providing an axis of rotation for the last dose sleeve 110, are rotatably fixed and are therefore rotatably engaged. Consequently, a rotation of the actuation member 30 leads to an equal rotation of the clutch 40 during a dose setting procedure. The clutch 40 is further connected with the drive sleeve 50. Hence, a distal portion of the clutch 40 is located inside the tubular shaped and hollow drive sleeve 50.

Here, and independent of the mode of operation of the drive mechanism 3, the clutch 40 and the drive sleeve 50 are axially fixed as well as rotatably fixed with respect to each other. Hence, a rotation of the clutch 40 is unalteredly transferred to the drive sleeve 50. Accordingly, also an axial displacement of the clutch 40 is unalteredly transferred to a respective axial displacement of the drive sleeve 50. The drive sleeve may for instance comprises two diametrically opposite longitudinal grooves in its inside facing sidewall, that are adapted to mate and to receive correspondingly shaped and radially outwardly extending ribs of the clutch 40.

Moreover, the clutch 40 comprises at least one or at least two oppositely located radially outwardly extending and resiliently deformable snap portions 46 adapted to engage with a correspondingly shaped recess 54 of the drive sleeve 50 as schematically illustrated in FIG. 1. By means of the mutually corresponding ribs 44 and grooves 52 as well as due to the snap portions 46 engaged with the recess 54, a rotational and longitudinal engagement of clutch 40 and drive sleeve 50 can be provided.

The drive sleeve 50 can be rotated inside and relative to the housing 20 in a dose incrementing direction 5 against the action of a helically shaped torsion spring element 58. One end, e.g. the proximal end of the helical spring 58 is attached and coupled to the proximal end of the drive sleeve 50 while an opposite, e.g. distal end of the helical spring 58 is fastened to the housing 20. A dose incrementing rotation of the actuation member 30 therefore leads to a corresponding rotation of the drive sleeve 50 against the restoring force of the helical spring 58 almost completely surrounding the drive sleeve 50.

Figure 4:
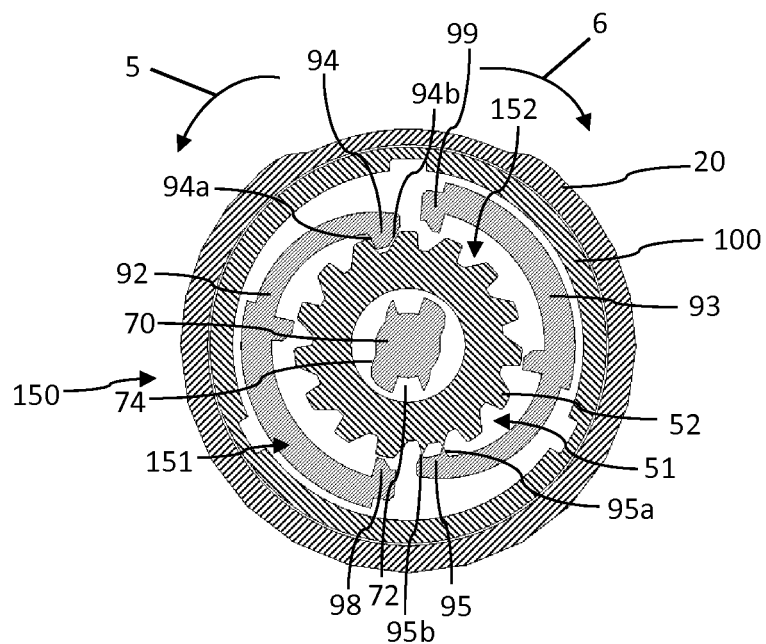
FIG. 4 is illustrative of a cross-section through the device according to FIG. 1 along C-C.

As shown in the cross-section of FIG. 4 the drive mechanism 3 is equipped with a particular ratchet mechanism 150 that may be generally implemented with a variety of different drive mechanism featuring a rotatable drive sleeve 50. As shown in FIG. 4, the drive sleeve 50 comprises a radially outwardly extending toothed profile 51 near a distal end section. The toothed profile 51 engages with mutually corresponding and radially inwardly extending first and second ratchet elements 94, 95 of first and second ratchet members 92, 93 of a first ratchet body 151, respectively. The first ratchet body 151 is fixed to the housing 20 and is integrally formed with a base member 90 that is fixedly attached to a distal end of the housing 20. The base member 90 further comprises radially inwardly extending protrusions 91 forming a through opening there between that coincides with the longitudinal axis 4 of the device 10 and which serves to axially guide the piston rod 70 relative to the base member 90 and hence relative to the housing 20.

Figure 4A:
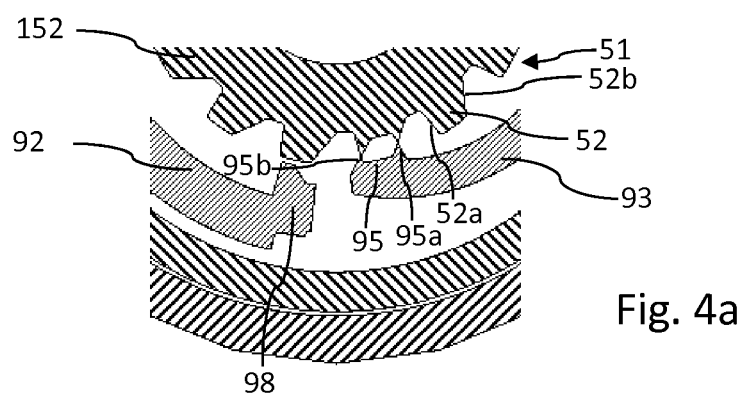
FIG. 4a shows an enlarged section of FIG. 4.
Figure 5:
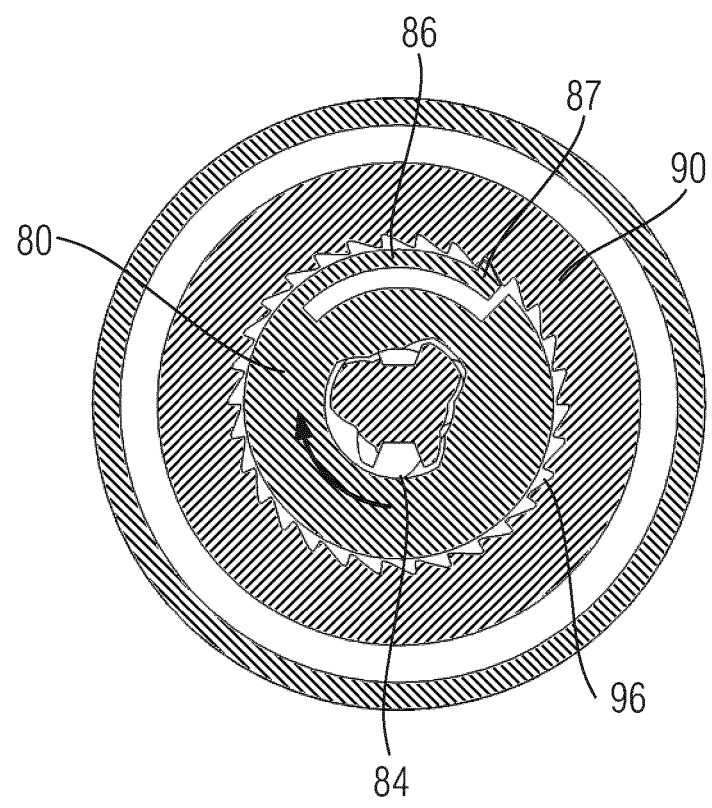
FIG. 5 shows a cross-section along D-D of the device according to FIG. 1.

The distal end of the drive sleeve 50 represents or comprises a second ratchet body 152 featuring a toothed profile 51. As indicated in FIG. 4, first and second ratchet elements 94, 95 of the first ratchet body 151 alternately engage with the toothed profile 51 of the drive sleeve 50 as the drive sleeve 50 is either rotated in dose incrementing direction 5 or in dose decrementing direction 6. As further indicated in the enlarged view of FIG. 4a, the first ratchet element 94 is somewhat triangular shaped and comprises a rather steep stop portion 94a facing in dose incrementing direction and being adapted to abut and to engage with a correspondingly shaped and rather steep edge 52a of the toothed profile 51.

When the drive sleeve 50 is rotated in dose incrementing direction 5 against the action of the spring element 58 the first ratchet element 94 regularly engages and meshes with consecutive teeth 52 of the drive sleeve 50. Since the stop portion 94a and the steep edge 52a of the first ratchet element 94 and the toothed profile 51 almost extend radially outwardly at a fairly steep angle a kind of a rotational interlock can be provided as the radially inwardly extending first ratchet element 94 with its stop portion 94a engages with a correspondingly shaped steep edge 52a of the toothed profile 51.

In a similar way also the second ratchet element 95 consecutively meshes or consecutively engages with the toothed profile 51 of the drive sleeve 50. Like the first ratchet element 94 also the second ratchet element 95 comprises a radially extending and hence a rather steep stop portion 95a facing in dose incrementing direction 5 to abut against the steep edge 52a of the toothed profile 51.

Adjacent to the stop portion 95a, the second ratchet element 95 comprises a radially inwardly extending tilted ramp portion 95b facing in dose decrementing direction 6 that engages with the ramp portion 52b of the toothed profile 51 facing in dose incrementing direction 5 when the drive sleeve 50 is rotated in dose incrementing direction 5.

The tipped and radially inwardly facing end of the ramp portion 95b may further mesh with the ramp portion 52b as the second ratchet body 152 is rotated in dose incrementing direction 5 relative to the first ratchet body 151. Here, the second ratchet element 95 provides a braking or retarding effect.

Likewise, also the first ratchet element 94 comprises a ramp portion 94b facing in dose decrementing direction 6 to engage and to mesh with the ramp portion 52b of the second ratchet body's 152 toothed profile 51.

The slope of the ramp portions 52b, 95b and 94b is adjusted and designed in accordance with the resilient properties of the arc-shaped and radially deformable ratchet members 92, 93. In this way, a well-defined mechanical interlocking of first and second ratchet elements 94, 95 with the toothed profile 51 can be obtained. By the geometric shape of ramp portions 52b, 94b and 95b mechanical resistance for dose incrementing or dose decrementing dialling of the drive sleeve 50 relative to the housing 20 can be adjusted whereas the geometric shape and position of the toothed profile's 51 steep edges 52a engaging with correspondingly shaped stop portions 94a, 95a of first and second ratchet elements 94, 95 may provide an adjustment of maximum holding and retention forces of respective torques between drive sleeve 50 and housing 20 that are required to overrule the ratchet mechanism 150 for dose correcting purpose.

As further illustrated in FIG. 4, first and second ratchet members 92, 93 each comprise a radially inwardly extending protrusion 98, 99 at an end portion opposite to the first and second ratchet elements 94, 95. These protrusions 98, 99 serve to radially guide and to radially fix the drive sleeve 50 inside the first ratchet body 150.

By rotating the drive sleeve 50 in a dose incrementing direction 5 the first ratchet element 94 of the first ratchet member 92 and the second ratchet element 95 of the second ratchet member 93 alternately engage and mesh with consecutive teeth 52 of the drive sleeve's 50 toothed profile 51. As illustrated in FIG. 4, the first and second ratchet elements 94, 95 of first and second ratchet members 92, 93 are circumferentially offset by e.g. half of a period of consecutively arranged teeth 52. In this way, the size of discrete steps for setting of a dose can be effectively reduced without the necessity to make use of respective small sized teeth 52 and ratchet elements 94, 95.

Additionally, the first and second ratchet elements 94, 95 also provide a retarding force acting on the rotating drive sleeve 50. In this way, a predefined braking or friction force can be applied to the drive sleeve 50 in order to at least partially compensate an impact of the spring element 58 on the rotational behaviour of the drive sleeve 50. Since the stop portions 94a, 95a differ in shape from the ramp portions 94b, 95b and since the steep edges 52a of the toothed profile differ in shape from ramp portions 52b retarding and holding forces of different magnitude can be provided when the drive sleeve is rotated in dose incrementing direction 5 and in dose decrementing direction 6. In this way a supporting effect of the helically shaped torsion spring element 58 on a dose decrementing rotation of the drive sleeve 50 can be counteracted or can be at least reduced.

A dose incrementing action governed by a rotation of the actuation member 30 and a corresponding rotation of the drive sleeve 50 also leads to a corresponding rotation of a dose indicating sleeve 100. The dose indicating sleeve 100 is threadedly engaged with the housing 20 and comprises numerous dose indications 104, typically in form of dose indicating numbers at its outer circumference, as for instance indicated in FIG. 10. The numbers are arranged in a helical way on the outer circumference of the dose indicating sleeve 100. Moreover, the dose indicating sleeve 100 comprises an outer thread engaged with the inside facing sidewall portion of the housing 20, in particular with the inner thread 28 of the housing 20 as indicated in FIG. 1.

A rotation of the drive sleeve 50 unalteredly transfers to a respective rotation of the dose indicating sleeve 100 by way of a keyed or splined engagement adapted to directly transfer a rotation the drive sleeve 50 to the dose indicating sleeve 100 and vice versa and supporting an axial displacement of the drive sleeve 50 relative to the dose indicating sleeve 100.

The drive sleeve 50 as indicated in FIG. 1 comprises an inner sleeve portion 55 with an inner or internal thread 59 to engage with the external thread 63 of the dose limiting member 60. Moreover, the drive sleeve 50 also comprises an outer sleeve portion 53 extending coaxially with the inner sleeve portion 55 and forming an annular and axially extending recess therebetween. Said recess is particularly adapted to receive the helical spring element 58. It is in particular the distal portion of the outer sleeve portion 53 which is keyed or splined engaged with the dose indicating sleeve 100. The outer sleeve portion 53 may comprise one or several radially outwardly extending ribs or protrusions to engage with correspondingly shaped and axially extending grooves 102 at an inside facing sidewall portion of the dose indicating sleeve 100 as shown for instance in FIG. 4. In this way the drive sleeve 50 and the dose indicating sleeve 100 are rotatably coupled but remain axially displaceable relative to each other.

When during a dose setting procedure the actuation member 30 is rotated relative to the housing 20 the drive sleeve 50 is rotated in the same way and due to the splined engagement of drive sleeve 50 and dose indicating sleeve 100 also the dose indicating sleeve 100 will always instantly show a corresponding dose size indicating number 104, e.g. representing an amount of international units IU in a dose displaying window 25 of the housing 20. As indicated for instance in FIG. 10, the dose indicating window 25 may comprise a recess or a through opening in the sidewall of the housing 20.

Decrementing of the dose, hence dialling the actuation member 30 in an opposite sense of rotation, leads to a respective counter-rotation of the drive sleeve 50. Consequently, also the dose indicating sleeve 100 rotates in the opposite sense, hence in a dose decrementing direction 6 and a correspondingly decreasing dose indicating number 104 will show up in the window 25.

In the following dispensing of a dose is described.

Once a dose has been set, the drive mechanism 3 may be switched into a dispensing mode by depressing the actuation member 30 in distal direction 1 as for instance indicated in FIG. 8. Here, the actuation member 30 actually fulfils a double or even a triple function. First of all, the actuation member 30 serves to transfer an angular momentum to the last dose sleeve 110 and/or to further functional components of the drive mechanism 3 operably engaged therewith. Second, the actuation member 30 controls and triggers a dose dispensing procedure. Third, the actuation member 30 actually seals and closes a proximal end of the housing 20 of the drive mechanism 3 and/or of the drug delivery device 10.

Moreover, the present arrangement of the actuation member 30 also allows for a priming of the drive mechanism 3 during manufacturing of the drug delivery device 10, when a cartridge 14 is to be readily arranged therein. In the process of assembly of the device 10, the piston rod 70 can be advanced in distal direction 1 to directly abut with the piston 16 of the cartridge 14. Here, a proximal end of the piston rod 70 is accessible, e.g. by means of a separate push rod, which is actually not illustrated here. It is then after bringing the piston rod 70 in operative engagement with the piston 16 of the cartridge 14 that the actuation member 30 is finally assembled to the housing 20 thereby closing the proximal receptacle 23 thereof.

By displacing the actuation member 30 in distal direction 1, the resilient spring elements 116 of the last dose sleeve 110 will be compressed. At the same time, the axially inwardly protruding journals 33 of the actuation member 30 will further extend through the longitudinal recesses 115 of the last dose sleeve 110 and will push a proximal rim 48 of the clutch 40 in distal direction 1 as becomes apparent from a comparison of FIGS. 7 and 8.

Figure 3:
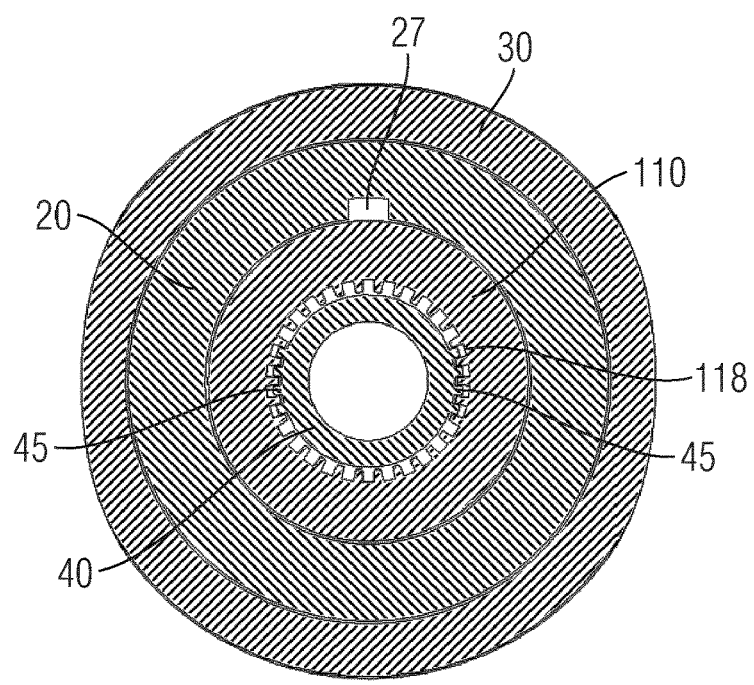
FIG. 3 shows a cross-section along B-B.

Due to this distally directed displacement of the clutch 40, radially outwardly extending teeth 45 of the clutch 40, as shown in FIG. 3, do no longer engage with the inner toothed surface 118 of the last dose sleeve 110. As a consequence, the clutch 40 is rotatably disengaged from the last dose sleeve 110 and is free to rotate.

At the same time radially inwardly extending teeth 34 provided at the inside facing sidewall portion of the actuation member 30 engage with a toothed ring 26 provided on the outer circumference of the proximal portion of the housing 20. Since the teeth 34 get in engagement with the toothed ring 26 by the axially and distally directed displacement of the actuation member 30 relative to housing 20, the actuation member 30 is rotatably locked to the housing 20 during a dose dispensing action. Consequently, the last dose sleeve 110, which is still rotatably engaged with the actuation member 30, cannot rotate during the dose dispensing procedure.

Since the clutch 40 is not only rotatably but also axially coupled and connected with the drive sleeve 50, the distally directed displacement of the clutch 40 is unalteredly transferred to a respective distally directed displacement of the drive sleeve 50.

As further indicated in FIG. 1, the clutch 40 is biased in proximal direction 2 by means of at least one spring element 21, which may be integrally formed with the housing 20. The spring element 21 can be resiliently deformed and biased in axial, hence distal direction 1 by the radially extending flange 49 of the clutch 40. Since the clutch 40 is to be displaced in distal direction 1 against the action of the spring element 21, a coupling of the drive sleeve 50 with a drive member 80 is only active as long as a respective distally directed force is applied to the actuation member 30, e.g. during a dose dispensing procedure. In particular, the member may comprise a drive nut.

The distally directed displacement of the drive sleeve 50 is limited by the drive member 80 as indicated in FIG. 1. When in mutual axial abutment, the drive sleeve 50 and the drive member 80 are rotatably engaged while the drive sleeve 50 with its toothed profile 51 is disengaged from the ratchet members 92, 93 of the base member 90. Mutual rotatable engagement of drive sleeve 50 and drive member 80 is achieved by mutually corresponding teeth or comparative interlocking members provided on a distal crown wheel 57 of the drive sleeve 50 and on a proximal crown wheel 82 of the drive member 80, respectively. Hence, the proximal face of the drive member 80 comprises a crown wheel 82 operable to engage with a correspondingly shaped crown wheel 57 provided on the distal face of the drive sleeve 50.

Typically, the axial extension of mutually corresponding crown wheels 82, 57 is such, that a rotational engagement of drive sleeve 50 and drive member 80 is achieved before the ratchet mechanism 151 between base member 90 and drive sleeve 50 is released due to a distally directed displacement of the drive sleeve 50 relative to the base member 90 and hence relative to the housing 20. In this way, a substantially slipless coupling of drive sleeve 50 and drive member 80 can be achieved.

An early or premature release of the actuation member 30 prior to a termination of the dose dispensing procedure will lead to an immediate proximally directed displacement of the clutch 40 relative to the housing 20 under the effect of the biased spring element 21. Consequently, the ratchet mechanism 151 will reengage thereby rotatable locking the drive sleeve 50 relative to the housing 20 and keeping the energy stored in the biased helical spring 58.

The drive member 80 is typically axially fixed in the base member 90 by means of a radially inwardly extending flange portion 97 as shown for instance in FIG. 1.

The base member 90 comprises two diametrically oppositely arranged and radially inwardly extending protrusions 91 that engage with correspondingly shaped grooves 72 of the piston rod 70. The piston rod 70 extends through the base member 90 in axial direction and comprises a pressure foot 71 at its distal end to directly engage with the piston 16 of the cartridge 14. The radially inwardly extending protrusions 91 of the base member 90 may further be part of a web or flange portion featuring a through opening, through which the piston rod 70 extends axially. The pressure foot 71 may be rotatable with respect to the piston rod 70. But when the piston rod 70 is non-rotatably engaged with the housing 20, a rotatably supported pressure foot 71 is not required in general.

The piston rod 70 comprises an outer thread 74 which is only threadedly engaged with an inner thread 84 of the drive member 80.

When rotatably coupled, the drive sleeve 50 under the action of the biased helical spring 58 transfers an angular momentum to the drive member 80, which in turn rotates around the axially fixed piston rod 70. The rotation of the drive member 80 then serves to advance the piston rod 70 in distal direction 1 for expelling of a dose of the medicament.

The drive member 80 also comprises a ratchet member 86 having a circumferentially extending arm resiliently deformable in radial direction. At the free end of the ratchet member 86 a radially outwardly extending tooth 87 is located which is adapted to mesh with a correspondingly shaped toothed surface or toothed profile 96 provided at the inside facing wall of the base member 90. As indicated in cross section in FIG. 5 the ratchet member 86 and the toothed structure 96 are configured such, that only a dose decrementing rotation 6 of the drive member 80 is allowed while a counter-directed rotation of the drive member 80 is effectively inhibited. This way, the piston rod 70 is only displaceable in distal direction 1 but not in proximal direction with respect to the housing 20. The ratchet member 86 of the drive member 80 and the toothed structure 96 of the base member 90 provide an effective anti-backup feature.

Moreover, when rotating in a dose decrementing direction during a dose dispensing procedure, the ratchet member 86, and in particular its radially outwardly extending free end consecutively meshes with the geared or toothed profile of the base member 90 or with a correspondingly shaped inner surface portion of the housing 20. The mutual engagement of the ratchet member 86 sliding along the toothed structure 96 also generates an audible click sound inherently indicating to the user, that the dispensing procedure is actually in progress.

For limiting a dose setting as well as a dose dispensing procedure the drive mechanism 3 further comprises a dose limiting member 60 slideably arranged on the piston rod 70 in axial direction and threadedly engaged with the drive sleeve 50. The dose limiting member 60 comprises the shape of a half-shell and therefore only partially surrounds the piston rod 70 in circumferential or tangential direction. The dose limiting member 60 comprises a radially inwardly extending gliding portion by way of which the dose limiting member 60 may slide or glide along the groove 72 of the piston rod 70. Due to the this mutual engagement of the gliding portion and the groove 72 of the piston rod 70, the dose limiting member 60 is rotatably fixed to the piston rod 70. In other words the dose limiting member 60 is splined to the piston rod 70 or is keyed engaged with the piston rod 70.

The dose limiting member 60 further comprises an external thread 63 at its outer circumference to engage with a correspondingly shaped internal thread 59 of the drive sleeve 50. In this way, the dose limiting member 60 is displaced axially with respect to the piston rod 70 as well as with respect to the drive sleeve 50 when the drive sleeve 50 rotates relative to the piston rod 70, in particular during a dose setting procedure.

During such a dose dispensing procedure, the drive sleeve 50 rotates in an opposite direction and hence the dose limiting member 70 experiences an oppositely directed axial displacement relative to the piston rod 70 and relative to the drive sleeve 50.

Typically, during a dose setting procedure, the dose limiting member 60 is displaced in proximal direction 2 towards the clutch 40. During a dose dispensing procedure, the dose limiting member 60 is displaced in the opposite direction, hence in distal direction 1 towards the drive member 80.

At its proximal end the dose limiting member 60 comprises a proximal stop portion extending from a proximal end face of the dose limiting member 60 in axial, hence proximal direction 2.

The proximal stop portion is adapted to abut with a correspondingly shaped and correspondingly oriented radially extending stop provided at a distal end of the clutch 40. By means of the mutual abutment of the proximal stop portion of the dose limiting member 60 with the stop located at the distal end of the clutch 40, a further rotation of the drive member 50 as well as of the clutch 40 relative to the piston rod 70 can be effectively inhibited.

Since the proximal stop portion of the dose limiting member 60 abuts in radial and circumferential direction with the clutch 40, any further rotation of the clutch 40 and hence any further rotation of the drive sleeve 50 rotatably coupled therewith is effectively blocked. Moreover, the clutch 40 may also provide a proximal stop for the dose limiting member 60. Due to the threaded engagement of the dose limiting member 60 and the drive sleeve 50, also here, a further rotation of the drive sleeve 50 exceeding a predefined maximum single dose configuration can be prevented. In this way, the dose limiting member 60 serves to provide a single dose limiting mechanism which is operable to effectively inhibit setting of a dose exceeding a predefined maximum single dose, e.g. 120 IU of insulin.

The dose limiting member 60 also comprises a distal stop portion extending accordingly in distal direction 1 from a distal end face of the dose limiting member 60. Here, the distal stop portion may accordingly engage with a radially inwardly and axially extending stop of the drive sleeve 50.

The position and orientation of the distal stop portion and the stop is selected such, that a mutual abutment of distal stop portion and stop is correlated with a zero dose configuration at the end of a dose dispensing procedure, i.e. when the dose indicating sleeve 100 has returned into its initial position.

Since the rotation of the drive sleeve 50 can be blocked and interrupted by the dose limiting member 60 in both directions, i.e. in a dose setting mode as well as in a dose dispensing mode, further stop features to inhibit a dose incrementing or dose decrementing rotation of the drive sleeve 50 are generally not required. As a consequence, even the dose indicating sleeve 100 and its arrangement in the housing 20 can be provided without any further rotation limiting means.

The distal stop portion of the dose limiting member 60 may be further equipped with a clicking member which is adapted to generate an audible sound before or when the distal stop portion engages with the corresponding stop of the drive sleeve 50. The clicking member typically comprises a resilient arm extending in circumferential direction from the distal stop portion. At its free end the arm comprises a latch portion featuring a tooth-like shape with a slanted or tilted leading surface. During a dose dispensing procedure and well before reaching the distal stop configuration, the latch portion engages with the stop and becomes subject to a axially, hence proximally directed evasive movement due to the resilient deformability of the arm.

In a final stop configuration the latch portion may relax and may snap into a recess provided at the inside wall of the drive sleeve 50, thereby generating an audible click sound. The returning of the latch portion and the resilient arm into its initial unbiased configuration may occur before the distal stop portion engages with the stop or it may coincide with the stop configuration, thereby audibly indicating to a user, that the dose dispensing procedure is close to end or has just terminated. Said audible feedback is not only obtained at the end of a dose dispensing procedure but also when a zero dose size, e.g. 0 IU is set by means of a dose correction procedure.

A last dose sleeve 110 as illustrated in FIGS. 7 to 9 comprises an outer thread 119 extending between a distal flange 111 and a proximal flange 113. The last dose sleeve 110 is further engaged, in particular threadedly engaged with a last dose member 120, which is of annular or arc-shape as illustrated in FIGS. 7 to 9. The last dose member 120 comprises an internal thread 128 to threadedly engage with the outer thread 119 of the last dose sleeve 110 and further comprises a radially outwardly extending protrusion 122 engaged with an axially extending groove 27 provided on the inside facing sidewall of the proximal receptacle 23 of the housing 20.

The groove 27 is also illustrated in the cross section A-A in FIG. 3. Since the protrusion 122 of the last dose member 120 engages with the groove 27 of the housing 20, the last dose member 120 is rotatably locked to the housing 20 and is therefore hindered to rotate with respect to the housing 20 in circumferential direction. Due to its threaded engagement with the outer thread 119 of the last dose sleeve 110, the last dose member 120 is displaced in axial direction 1 when the last dose sleeve 110 is rotated with respect to the housing 20.

Typically, the last dose member 120 comprises a leading edge and a trailing edge in circumferential direction with respect to the sense of rotation relative to the last dose member 120. By means of its leading and/or trailing edges the last dose member 120 is engageable with radially extending or radially protruding stop portions provided on the outer circumference of the last dose sleeve 110 adjacent to its proximal and distal flanges 113, 111, respectively, when reaching a last dose limiting configuration.

When the leading or trailing edge of the last dose member 120 abuts or engages with the at least one stop of the last dose sleeve 110, further rotation of the last dose sleeve 110 can be effectively blocked and inhibited, thereby blocking or inhibiting a further dose incrementing rotation of the actuation member 30 during a dose setting procedure. The radially extending leading or trailing edges of the last dose member 120 and the correspondingly shaped stops of the last dose sleeve 110 are adapted to immediately block a further rotation of the last dose sleeve 110 and hence of the actuation member 30 when a predetermined rotational position of the last dose sleeve 110 and the actuation member 30 has been reached.

The thread 119 and the axial dimensions of the last dose sleeve 110 are selected such, that an axial position of the last dose member 120 on the last dose sleeve 110 is directly correlated to the axial position of the piston rod 70 and hence to the axial position of the piston 16 in the cartridge 14.

It is to be mentioned here, that the last dose limiting mechanism implemented by the last dose sleeve 110 is beneficial in that the last dose sleeve 110 is directly located inside the actuation member 30. In effect, a tolerance chain between the actuation member 30 and the last dose limiting mechanism is fairly short and can therefore be reduced to a minimum.

Moreover, the flexibility of the various parts, of which the drive mechanism 3 is assembled may play a subordinate role, as the flux of force from the actuation member 30 to the last dose sleeve 110 is comparatively short. Moreover, also from a user's point of view, the position of the last dose sleeve 110 together with the last dose member 120 inside the actuation member 30 will provide a rather solid, robust and therefore very reliable last dose limiting mechanism.

In the embodiment as illustrated in FIG. 1 the housing comprises a substantially tubular shaped body 20 that is closed in proximal direction by a closure member 130 fixedly attached to the proximal end of the housing's body 20. The closure member 130 comprises a cup-shaped cylindrical sidewall portion 132 featuring a radially inwardly extending fastening member 133 to engage with a correspondingly shaped recess of the proximal housing 20. Alternatively the closure member 130 and the body 20 may also be integrally formed as a single piece and may form a proximal housing 20. In the present context body and housing may be synonyms.

Figure 10:
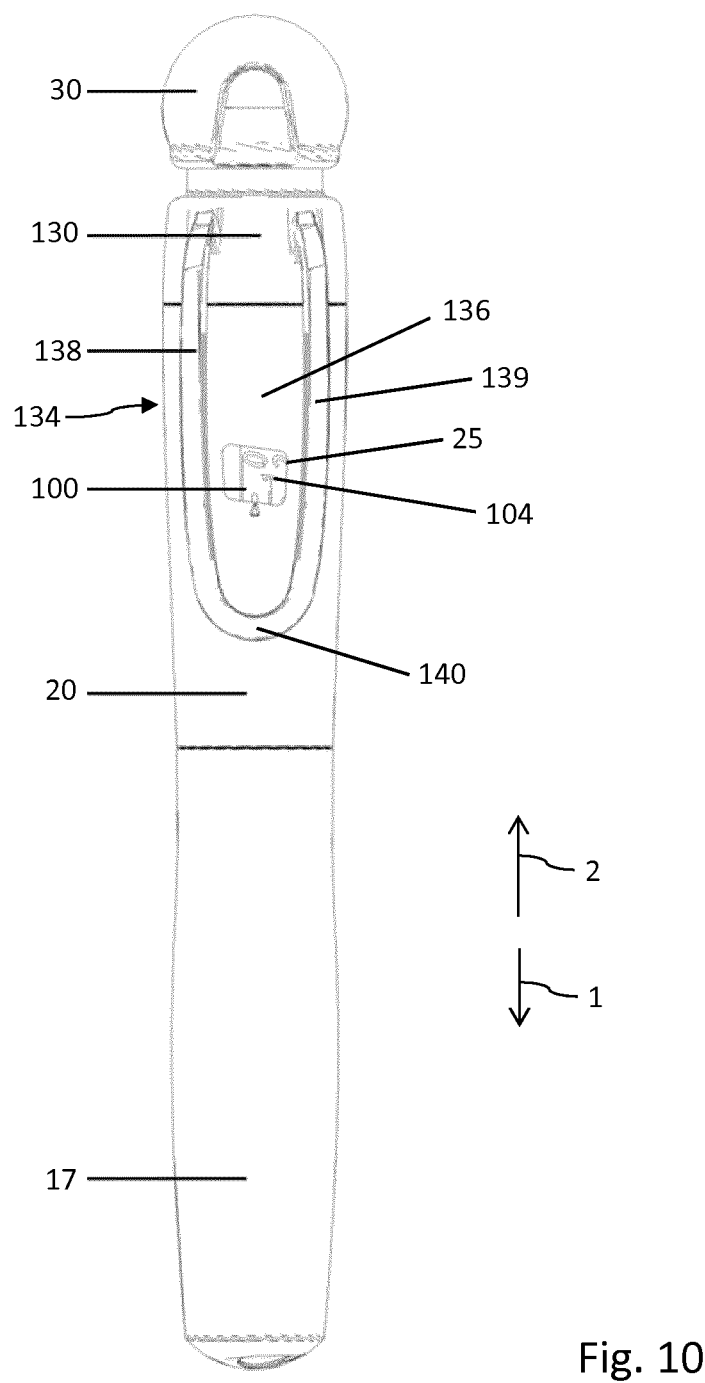

As becomes apparent from FIG. 10, the proximal housing 20 is further provided with a fastening member 134 that in the present embodiment is designed as a fixing clip. Said fixing clip or fastening member 134 is integrally formed with the closure member 130 and extends from the proximal end of the housing 20 in distal direction 1. Apparently the fastening member 134 is arranged at the outer surface of the housing's body 20 and extends adjacent to the dose indicating window 25. Moreover, the fastening member 134 comprises a recess 136 substantially overlapping with the dose indicating window 25 of the housing 20. In this way the dose indicating numbers 104 showing up in the dose indicating window 25 are discernible through the fastening member 134.

In the embodiment as illustrated in FIG. 10 the fastening member 134 comprises two circumferentially separated but substantially parallel extending branches 138, 139 that mutually merge via a distal connecting section 140 forming a bridging portion between the two branches 138, 139. In this way the fastening member 134 comprises a U-shape and forms a recess 136 between the lateral branches 138, 139.

Alternatively it is also conceivable, that the fastening member 134 is made of a single fixing clip-like branch extending across the dose indicating window 25 but featuring a transparent section overlapping with the dose indicating window 25.

By means of the fastening member 134 arranged in an overlapping configuration with the dose indicating member 25, the dose indicating member 25 can be protected against environmental influences, such like mechanical impact. Moreover, the fastening member 134 radially outwardly extending along the proximal housing 20 provides a kind of roll-away protection, e.g. when the tubular shaped drug delivery device 10 is for instance positioned on a table. The radially outwardly extending fastening member 134 effectively prevents unlimited rolling motion of the housing 20 and therefore provides an additional security feature for the drug delivery device.

Moreover, and in contrast to embodiments, where a fastening member is provided on the protective cap 17 the fastening member 134 according to the embodiment of FIG. 10 allows for a direct fastening of the housing 20 to e.g. a piece of cloth or to a pocket of a user. Even in the event that the protective cap 17 would inadvertently release from the housing 20, the housing 20 and hence almost the entire drug delivery device 10 would remain fastened to the respective piece of cloth.

It is to be noted that the fastening member 134 is universally applicable with a variety of different drug delivery devices 10 and drive mechanisms 3 that feature at least a dose indicating window 25 in a housing 20.

The invention claimed is:

1. A drive mechanism of a drug delivery device for dispensing of a dose of a medicament, the drive mechanism comprising:
    an elongated housing;
    a piston rod to operably engage with a piston of a cartridge to displace the piston of the cartridge in a distal direction;
    a drive sleeve rotatably supported in the housing at least in a dose incrementing direction against an action of a spring element; and
    a ratchet mechanism to rotatably fix the drive sleeve relative to the housing, the ratchet mechanism comprising a first ratchet body and a second ratchet body, wherein the first ratchet body has a first ratchet element and a second ratchet element to alternately engage with a toothed profile of the second ratchet body;
    wherein one of the first ratchet body and the second ratchet body is operably engaged with the housing and another of the first ratchet body and the second ratchet body is operably engaged with the drive sleeve, and
    wherein the first ratchet element is phase shifted to the second ratchet element with regard to a period of the toothed profile of the second ratchet body, and wherein the first ratchet body and the second ratchet body are axially displaceable relative to each other to selectively engage and to selectively disengage the first ratchet body and the second ratchet body.

2. The drive mechanism according to claim 1, wherein the first ratchet body comprises a first ratchet member and a second ratchet member, and wherein the first ratchet member supports the first ratchet element and the second ratchet member supports the second ratchet element.

3. The drive mechanism according to claim 2, wherein the first ratchet element and the second ratchet element are located at opposite circumferential end sections of the first ratchet member and the second ratchet member extending along the toothed profile of the second ratchet body.

4. The drive mechanism according to claim 2, wherein at least one of the first ratchet member or the second ratchet member is pivotable, resiliently deformable, or both pivotable and resiliently deformable in a radial direction.

5. The drive mechanism according to claim 2, wherein the first ratchet member and the second ratchet member are symmetrically shaped, symmetrically arranged, or both symmetrically shaped and symmetrically arranged, with respect to a longitudinal axis of the drive sleeve.

6. The drive mechanism according to claim 1, wherein a position and a geometrical shape of the first ratchet element and the second ratchet element are such that one of the first ratchet element and the second ratchet element is engaged with the toothed profile of the second ratchet body while another of the first ratchet element and the second ratchet element is disengaged from the toothed profile of the second ratchet body and vice versa.

7. The drive mechanism according to claim 1, wherein at least one of the first ratchet element or the second ratchet element is adapted to block a rotation of the second ratchet body relative to the first ratchet body in a dose decrementing direction when a torque acting between the first ratchet body and the second ratchet body is below a first predefined threshold.

8. The drive mechanism according to claim 1, wherein at least one of the first ratchet element or the second ratchet element is adapted to release a rotation of the second ratchet body relative to the first ratchet body in a dose decrementing direction when a torque acting between the first ratchet body and the second ratchet body is equal to or above a first predefined threshold.

9. The drive mechanism according to claim 1, wherein at least one of the first ratchet element or the second ratchet element is adapted to apply a retarding force of predefined magnitude onto the second ratchet body when the second ratchet body rotates relative to the first ratchet body in at least one of the dose incrementing direction or a dose decrementing direction.

10. The drive mechanism according to claim 1, wherein the first ratchet element and the second ratchet element are arranged at diametrically opposite portions of the toothed profile of the second ratchet body.

11. The drive mechanism according to claim 1, wherein the first ratchet body is fixed to the housing or is integrally formed with the housing and comprises the first ratchet element and the second ratchet element extending radially inwardly and wherein the second ratchet body is fixed to the drive sleeve or is integrally formed with the drive sleeve and wherein the toothed profile of the second ratchet body extends radially outward.

12. The drive mechanism according to claim 1, wherein the first ratchet body is fixed to the drive sleeve or is integrally formed with the drive sleeve and comprises the first ratchet element and the second ratchet element extending radially outwardly, and wherein the second ratchet body is fixed to the housing or is integrally formed with the housing and wherein the toothed profile of the second ratchet body extends radially inwardly.

13. A drug delivery device for dispensing of a dose of a medicament, the drug delivery device comprising:
an elongated housing;
a cartridge at least partially filled with the medicament and being arranged in the housing;
a piston rod to operably engage with a piston of the cartridge to displace the piston of the cartridge in a distal direction;
a drive sleeve rotatably supported in the housing at least in a dose incrementing direction against an action of a spring element; and
a ratchet mechanism to rotatably fix the drive sleeve relative to the housing, the ratchet mechanism comprises a first ratchet body and a second ratchet body, wherein the first ratchet body has a first ratchet element and a second ratchet element to alternately engage with a toothed profile of the second ratchet body;
wherein one of the first ratchet body and the second ratchet body is operably engaged with the housing and another of the first ratchet body and the second ratchet body is operably engaged with the drive sleeve, and
wherein the first ratchet element is phase shifted to the second ratchet element with regard to a period of the toothed profile of the second ratchet body and wherein the first ratchet body and the second ratchet body are axially displaceable relative to each other to selectively engage and to selectively disengage the first ratchet body and the second ratchet body.

14. The drug delivery device according to claim 13, further comprising a cartridge holder fixed to the housing, wherein the cartridge is arranged in the cartridge holder.

15. A method of operating a drug delivery device, the method comprising:
rotating a drive sleeve in a dose incrementing direction against an action of a spring element to set a dose to be dispensed, thereby causing ratchet elements of a first ratchet body to alternately engage with a second ratchet body; and
releasing the spring element to dispense the dose, wherein causing the ratchet elements to alternately engage with the second ratchet body comprises
causing a first ratchet element of the ratchet elements to engage a toothed profile of the second ratchet body while a second ratchet element of the ratchet elements is disengaged from the toothed profile of the second ratchet body, wherein the first ratchet element is phase shifted to the second ratchet element with regard to a period of the toothed profile of the second ratchet body,
causing the second ratchet element of the ratchet elements to engage the toothed profile of the second ratchet body while the first ratchet element of the ratchet elements is disengaged from the toothed profile of the second ratchet body, and
causing one of the first and second ratchet bodies to be axially displaced relative to another one of the first ratchet body and the second ratchet body to disengage the first ratchet body from the second ratchet body.

16. The method according to claim 15, wherein rotating the drive sleeve causes the second ratchet body to rotate such that the ratchet elements of the first ratchet body alternately engage the second ratchet body, the second ratchet body being operably engaged to the drive sleeve.

17. The method according to claim 15, wherein rotating the drive sleeve in the dose incrementing direction causes the ratchet elements of the first ratchet body to alternately block the drive sleeve from rotating in a dose decrementing direction.

18. A drive mechanism of a drug delivery device for dispensing of a dose of a medicament, the drive mechanism comprising:
an elongated housing;
a piston rod to operably engage with a piston of a cartridge to displace the piston of the cartridge in a distal direction;

a drive sleeve rotatably supported in the housing at least in a dose incrementing direction against an action of a spring element; and a ratchet mechanism to rotatably fix the drive sleeve relative to the housing, the ratchet mechanism comprising a first ratchet body and a second ratchet body, wherein the first ratchet body has a first ratchet element and a second ratchet element to alternately engage with a toothed profile of the second ratchet body;

wherein one of the first ratchet body and the second ratchet body is fixed to the housing and another of the first ratchet body and the second ratchet body is operably engaged with the drive sleeve, and wherein the first ratchet body and the second ratchet body are axially displaceable relative to each other to selectively engage and to selectively disengage the first ratchet body and the second ratchet body.

19. A drive mechanism of a drug delivery device for dispensing of a dose of a medicament, the drive mechanism comprising:

an elongated housing;

a piston rod to operably engage with a piston of a cartridge to displace the piston of the cartridge in a distal direction;

a drive sleeve rotatably supported in the housing at least in a dose incrementing direction against an action of a spring element; and a ratchet mechanism to rotatably fix the drive sleeve relative to the housing, the ratchet mechanism comprising a first ratchet body and a second ratchet body, wherein the first ratchet body has a first ratchet element and a second ratchet element to alternately engage with a toothed profile of the second ratchet body;

wherein one of the first ratchet body and the second ratchet body is operably engaged with the housing and another of the first ratchet body and the second ratchet body is operably engaged with the drive sleeve; and wherein a position and a geometrical shape of the first ratchet element and the second ratchet element are such that one of the first ratchet element and the second ratchet element is engaged with the toothed profile of the second ratchet body while another of the first ratchet element and the second ratchet element is disengaged from the toothed profile of the second ratchet body, and such that another of the first ratchet element and the second ratchet element is engaged with the toothed profile of the second ratchet body while the one of the first ratchet element and the second ratchet element is disengaged with the toothed profile of the second ratchet body, and wherein the first ratchet body and the second ratchet body are axially displaceable relative to each other to selectively engage and to selectively disengage the first ratchet body and the second ratchet body.

20. The drive mechanism according to claim 1, wherein the first ratchet element and the second ratchet element are circumferentially offset by a half of a period of consecutively arranged teeth, and the first ratchet element and the second ratchet element are longitudinally aligned with one another.

\* \* \* \* \*